United States Patent [19]

Deurer et al.

[11] Patent Number: 5,698,216
[45] Date of Patent: Dec. 16, 1997

[54] TRANSDERMAL THERAPEUTIC SYSTEM FOR THE ADMINISTRATION OF PHYSOSTIGMINE TO THE SKIN AND PROCESS FOR THE PRODUCTION THEREOF

[75] Inventors: Lothar Deurer, Koblenz; Thomas Hille, Neuwied; Thomas Profitlich, Munich; Fritz Stanislaus, Munich; Kersten Walter, Munich, all of Germany

[73] Assignee: LTS Lohmann Therapie-Systeme GmbH & Co., Neuwied, Germany

[21] Appl. No.: 433,459

[22] PCT Filed: Oct. 27, 1993

[86] PCT No.: PCT/EP93/02970

§ 371 Date: Jul. 12, 1995

§ 102(e) Date: Jul. 12, 1995

[87] PCT Pub. No.: WO94/10999

PCT Pub. Date: May 26, 1994

[30] Foreign Application Priority Data

Nov. 12, 1992 [DE] Germany ............... 42 38 223.8

[51] Int. Cl.$^6$ ............................................. A61F 13/02
[52] U.S. Cl. ............ 424/448; 424/447; 424/449
[58] Field of Search ........................ 424/448, 449, 424/447

[56] References Cited

U.S. PATENT DOCUMENTS

| | | | |
|---|---|---|---|
| 5,370,924 | 12/1994 | Kochinke | 428/244 |
| 5,391,375 | 2/1995 | Hille | 424/449 |

FOREIGN PATENT DOCUMENTS

| | | |
|---|---|---|
| 2163347 | 2/1986 | United Kingdom . |
| 2171906 | 9/1986 | United Kingdom . |
| 9112785 | 9/1991 | WIPO . |
| 9115176 | 10/1991 | WIPO . |

OTHER PUBLICATIONS

Salway, J. Chem. Soc. (London) 101, pp. 978–989 (1912).

*Primary Examiner*—D. Gabrielle Phelan
*Attorney, Agent, or Firm*—Wenderoth, Lind & Ponack

[57] ABSTRACT

A transdermal therapeutic system for the administration of physostigmine to the skin, consisting of a backing layer impermeable to active substance, a pressure-sensitive reservoir layer containing 40 to 90%-wt. polymeric material and 0.1 to 20%-wt. physostigmine base or one of the pharmaceutically acceptable salts thereof, and of a detachable protective layer covering the reservoir layer, comprises in its reservoir layer acrylate- and/or methacrylate-based polymeric material and 0.1 to 40%-wt. of a softener containing the hydroxyl group with an HLB value between 1.1 and 12.0.

9 Claims, No Drawings

TRANSDERMAL THERAPEUTIC SYSTEM FOR THE ADMINISTRATION OF PHYSOSTIGMINE TO THE SKIN AND PROCESS FOR THE PRODUCTION THEREOF

This application is a 371 of PCT/EP93/02970, filed Oct. 27, 1993.

The invention relates to a transdermal therapeutic system containing physostigmine as active component, and to a process for the production thereof.

The application of physostigmine, for example for the treatment of Alzheimer's disease has been described in the literature several times, whereby the efficacy of the substance was judged differently. Since the alkaloid exhibits a high first pass effect—the bioavailability of physostigmine after oral administration is in the range of 5%—the differing results must be attributed to different forms of application.

DE-OS 35 28 979 describes a composition which in addition to physostigmine contains a medium-chain carboxylic acid; this composition can be applied on a bandage, an insert or a compress, which are applied by means of a dressing. With this kind of application, which is not a TTS per se, it is intended to provide the bandage, compress or insert with an inner reservoir layer, an impermeable protective barrier foil or an impermeable protective film and to apply a diffusion controlling membrane between the reservoir and the skin. Neither the diffusion controlling membrane nor the protective foils are described in detail. The carboxylic acids are explicitly mentioned to be effective carriers for the administration of the pharmaceutic through the skin which otherwise would not be able to penetrate through the skin barrier. However, this statement is not tenable from the scientific point of view. DE-PS 36 06 892 describes a retarded application of physostigmine and other active substances, which application may be carried out transdermally. A special formulation is not disclosed. What is more, reference is made to a pre-described formulation (U.S. Pat. No. 3,921,363).

A further publication describing the application of physostigmine is WO 91/15176. This publication does not go beyond the teaching of the German Patent DE 38 43 239 discussed hereinbelow. Apart from the only vague statements concerning the transdermal therapeutical systems, neither of the two publications mentioned hereinabove deal with the instability of physostigmine, which instability was realized very early. In this respect, however, reference may be made, for example, to the following literature dealing with the instability of physostigmine: (Eber, W., Pharmaz. Ztg. 37, 483 (1888), Herzig, J., Mayer, H., Mh. Chem. 18, 379 (1897); Herzig, J., Lieb, H., ibidem 39, 285 (1918); Salway, A. A., J. Chem. Soc. (London) 101, 978 (1912)).

Owing to a rapid decomposition of the active substance, this instability severely limits the use of physostigmine in pharmaceutics.

The problem of the rapid decompostion of physostigmine in a TTS is also dealt with in DE 38 43 238 and DE 38 43 239. The TTS described in DE 38 43 239 exclusively contains lipophilic softeners, whereas the system described in DE 38 43 238, apart from lipophilic softeners, contains carboxylic acids with rather long chains, viz oleic acid or undecene acid, as solvents for physostigmine. These fatty acids, as well, are lipophilic substances. Thus, the two systems have in common that physostigmine is released to the skin from a lipophilic matrix securing the stability of the active substance.

Surprisingly, it was found by way of controls that TTS prepared according to the teachings of the patent specifications DE 38 43 238 and DE 38 43 239 do not satisfactorily meet the strict requirements which must be applied to the self-adhesiveness of a TTS. Tests in which the TTS were worn brought the result that in the case of some of the test persons the TTS, after having been worn for only 8 hours, did no longer adhere with their entire surface. After 24 hours, 10% of the test persons had lost the TTS, and in the case of 15% of the test persons there was no longer an all-over skin contact. Only in the case of 75% of the test persons was the adhesive behaviour of the TTS satisfactory. However, TTS which adhere only with 75% of the test persons or patients without giving cause for complaints do not fulfil the strict requirements that must be applied to therapeutic systems. By definition, a transdermal therapeutic system contains one or more drugs which are released at a pre-determined rate, continuously, over a pre-determined period of time, to a pre-determined application site ("Heilmann, Klaus: Therapeutische Systeme—Konzept und Realisation programmierter Arzneiverabreichung", 4th edition, Ferdinand Enke Verlag Stuttgart, 1984, p. 26). Without permanent skin contact over the predetermined period of time, physostigmine cannot be released in a controlled manner, which puts the desired therapy in question or seriously endangers it, respectively.

It is known to the man skilled in the art that the adhesive behaviour of a TTS improves with increasing polarity of the softener incorporated into the system.

In the following experimental part it will be shown that—although there are exceptions—the adhesive force of the TT systems manufactured in accordance with the invention is the greater, the greater the hydrophilicity of the matrix. As a measure for the hydrophilicity, the hydrophilicity of the softeners employed, viz that of alcohols, was used.

A further measure for the hydrophilicity of the softeners is their HLB value, which may be calculated according to the following formula:

$$HLB = 20\left(1 - \frac{Mo}{M}\right)$$

$Mo$ = molecular mass of the hydrophobe portion
$M$ = total molecular mass and for esters:

$$HLB = 20\left(1 - \frac{SV}{AN}\right)$$

$SV$ = saponification value of the ester
$AN$ = acid number of the separated fatty acid (quotation from Voigt, Rudolf: Lehrbuch der pharmazeutischen Technologie, 3rd revised edition, Verlag Chemie, Weinheim, New York 1979, p. 352)

The HLB values of the softeners are shown in Table 5.

Since softeners split physostigmine hydrolytically, it is necessary to formulate such matrices as are, on the one hand, hydrophilic, owing to the use of special polar softeners, and which, on the other hand, prevent the hydrolysis of the active substance owing to the provision of particularly suitable polymer components.

It is thus the object of the invention to provide a TTS releasing physostigmine or one of the pharmaceutically acceptable salts thereof over a period of time of at least 12 hours, in a controlled manner, securing a durable fixation of the plaster, over its entire surface, to the human body, and at the same time ensuring that the physostigmine contained in the system is not decomposed in a manner altering the therapeutic effect.

This object is achieved in accordance with the invention by means of a transdermal therapeutic system according to the invention.

In this connection, the backing layer impermeable to active substance may consist of flexible or inflexible material. Materials which can be used for the production of said layer are polymer films or metal foils, such as aluminium foil, used singly or coated with a polymer substrate. Also, textile fabrics may be used, if the components of the reservoir cannot penetrate through the same owing to their physical properties. In a preferred embodiment, the backing layer is a composite material made of an aluminized foil.

A process for the production of the TTS is also provided.

The reservoir layer consists of a pressure-sensitive polymer matrix and contains the active substance physostigmine or the pharmaceutically acceptable salts thereof, the softener and, as may be required from case to case, additives.

When selecting the substances for the construction of the reservoir, the following requirements must be simultaneously fulfilled:

The physostigmine, which is comparatively unstable, must not be split by hydrolysis nor attacked by oxidation during storage or therapy.

The reservoir layer must exhibit good adhesive behaviour towards the skin over the entire period during which the TTS is to be worn, at least 12 hours.

These conditions are surprisingly fulfilled by combining the base polymers and softeners described according to the invention, the selection of the base polymer being dependent on the chemical and physical properties of the physostigmine and having to fulfil the requirement that the matrix be sufficiently hydrophilic to secure adhesive force when the TTS is being worn.

In this connection, the invention starts out from the finding that it is not the polymers but the softeners that split physostigmine hydrolytically. For this reason, the hydrophilicity of the softeners must not exceed a certain limit.

Solvents such as, for example, methanol, ethanol and isopropanol, which are not softeners in the sense of the invention, admittedly have HLB values within the limits of the invention; however, they do cause the cleavage of physostigmine. For this reason, they must not be used in the reservoir layer of the matrix.

Alcohols having extremely low HLB values, e.g. heptadecanol, nonadecanol and eicosanol, are not capable of splitting physostigmine, it is true, but they lead to a poorer adhesive behaviour of the system, and thus constitute no improvement over the triglycerides of the medium-chain fatty acids.

The hydrophilicity of the matrix required for the active substance flow through the skin must consequently be realized by using polymers having polar functional groups, such as hydroxyl, carbonyl, carboxyl or amino groups.

Suitable polymers are, for example, polyacrylates or polymethacrylates having the aforementioned polar functional groups.

Without limiting the invention, acrylate-based acrylate copolymers of 2-ethylhexyl acrylate, vinyl acetate and acrylic acid with or without titanium or aluminium chelate esters, respectively, are preferred. Preferred methacrylates are copolymers on the basis of dimethylaminoethyl methacrylates and neutral methacrylic esters.

Examples for softeners according to the invention are higher alcohols, as they are, on the one hand, sufficiently hydrophile to form the required "hydrophile matrix" with the above-described polymers, but, on the other hand, are not polar enough to split physostigmine in the systeme via alcoholysis. Linear or branched, saturated or unsaturated alcohols with 6 to 20 carbon atoms have proved particularly successfull.

The kind of possible other additives is dependent on the polymer, softener and active substance employed: According to their function, they can be divided into tackifiers, stabilizers, carriers, diffusion and penetration regulating additives, or fillers. Without limiting the invention, as fillers, polymers selected from the groups of the polyvinyl pyrrolidones are mentioned. Other physiologically acceptable substances suitable for this purpose are known to the man skilled in the art.

The removable protective layer, which is in contact with the reservoir layer and is removed prior to application, consists, for example, of the same materials as are used for the manufacture of the backing layer, provided that they are rendered detachable, for example, by way of a silicone treatment.

Other detachable protective layers are, for example, polytetrafluoroethylene, treated paper, cellophane, polyvinyl chloride, and the like. Where the laminate according to the invention is divided into sizes (plasters) suitable for therapy, the dimensions of the protective layer may have a protruding end, so that they may be stripped off the plaster more easily.

Proof of the stability conditions of physostigmine: In comparison example 1, triglycerides of medium-chain fatty acids, DAB 9 [=the German Pharmacopoeia, 9th edition] (neutral oil), HLB value 1, are used as softeners, since these softeners, according to the teaching of DE 38 43 239 guarantee the stability of physostigmine. This can be proved by way of experiments. In the other examples, softeners selected from the compound group of alcohols (branched or linear, saturated or unsaturated) with 6 to 20 carbon atoms are used. Surprisingly, in this case also, the stability of the physostigmine in the TTS is successfully proved by means of experiments although in a compatibility test physostigmine is hydrolytically split by these compounds. For this purpose, samples of about 50 mg physostigmine base and about 100 mg alcohol each were stored for three weeks, at 40° C. in an HPLC vessel, under exclusion of light and air.

Subsequently, 1 ml chloroform is added to each of the samples and the colour is assessed. Thereafter, the samples were examined by thin-layer chromatography.

The TLC conditions are as follows:

| | |
|---|---|
| Absorbent: | silica gel TLC glass plate 60 F 254 |
| Solvent: | chloroform:acetone:diethylamine 5:4:1 |
| Chamber saturation: | 2 h |
| Flow time: | 35 min |
| Amount applied: | 5 µl |
| Detection: | 1. UV light 254 nm |
| | 2. iodine chamber |

The results are shown in the following Table 1.

TABLE 1

| 50 mg Physostigmine + 100 mg "softener" | Colour | TLC-Evaluation: Decomposition product detectable |
|---|---|---|
| 1. triglycerides of medium-chain fatty acids | colourless | − |
| 2. methanol | dark red | ca. 20% |
| 3. ethanol | dark red | ca. 15% |
| 4. isopropanol | dark red-red | ca. 15% |
| 5. 1-hexanol | dark red-red | + |
| 6. 1-heptanol | red | + |
| 7. 1-octanol | bright red | + |
| 8. 1-nonanol | bright red | + |

TABLE 1-continued

| 50 mg Physostigmine + 100 mg "softener" | Colour | TLC-Evaluation: Decomposition product detectable |
|---|---|---|
| 9. 1-decanol | bright red | + |
| 10. 1-undecanol | bright red | – |
| 11. 1-dodecanol | bright red | + |
| 12. 1-tetradecanol | colourless-bright red | in traces |
| 13. 1-pentadecanol | colourless-bright red | in traces |
| 14. 1-heptadecanol | colourless | in traces |
| 15. 1-nonadecanol | colourless | – |
| 16. 1-eicosanol | colourless | – |
| 17. 2-octyldodecanol (1) | colourless | – |
| 18. oleyl alcohol | yellow | – |

Evaluation of the colours:

Since the decomposition products of physostigmine are coloured, only those solutions can be considered stable which remain colourless (Nos. 1 and 14–17). At the same time, the degree of decomposition can be inferred from the intensity of the change in colour.

The TTS were produced according to the following method: The transdermal therapeutic system according to the invention is manufactured preferably by homogeneously admixing the active substance with the components of the pressure-sensitive reservoir layer, optionally in solution, and is spread onto the backing layer impermeable to active substance, whereafter the solvent or solvents, where present, is/are removed. Subsequently, the adhesive layer is provided with a suitable protective layer.

The invention is further illustrated by the following examples:

Example 1 (Comparison example)

238 g of a self-crosslinking, acid (acid number of the dried mass ca. 40) acrylate copolymer of 2-ethylhexyl acrylate, vinyl acetate and acrylic acid (47,85% in a solvent mixture of isopropanol, ethyl acetate, heptane, toluol and acetyl acetone 26:37:32:4:1), 50 g triglycerides of the caprylic/capric acids, 16 g physostigmine base and 20 g ethyl acetate are mixed while stirring.

Then 20 g of a cationic copolymerisate on the basis of dimethylaminoethyl methacrylate and neutral methacrylic esters, are strewn into the mixture while stirring. Under elimination of light the mixture is stirred for 8 hours at room temperature until complete dissolution and the resulting solution is coated by means of a coating knife onto an aluminized and siliconized polyethylene film.

After removal of the solvent by drying for 20 minutes at 60° C., the adhesive film is covered with a polyester film of 15 μm. Using appropriate cutting tools, a size of 10 cm$^2$ is punched out and the latticed edges are removed.

The stability of the active substance in the system was shown by way of content determinations immediately after the manufacture and after 3-months' storage, respectively. In this connection, neither the decomposition products eseroline and rubreserine, known from the literature, nor other decomposition products which have so far not been described, could be detected. The physostigmine content corresponded to the theoretical value. The method used was as follows:

Preparation of the samples:

1 plaster with covering foil is divided into four parts by means of a pair of scissors; the covering foil is removed and is shaken, together with the plaster sections, for at least 2 hours in a glass vessel which is capable of being closed and is protected from light, with 50,0 ml tetra-hydrofurane (p.a.), then subjected to ultrasonic treatment for 10 min and subsequently centrifuged. Dilution for HPLC with methanol; and further centrifugation. Thereafter, the content of physostigmine in the centrifugate is determined by HPLC.

Example 1 has a lipophilic matrix, due to the use of triglycerides. It was chosen in order to obtain a standard the stability of which could be used as a measure for the stability of examples 2–17.

Examples 2–17 were prepared according to the same method as example 1. Instead of neutral oil DAB 9, higher alcohols with 6 to 20 carbon atoms were used as softeners. Examples 15 and 16 are not examples in accordance with the present invention. When using these alcohols, decomposition of the physostigmine occurs.

The qualitative and quantitative compositions of the matrices after removal of the solvent are shown in Table 2 hereinbelow. After manufacture and after storage at 25° C. and 40° C., respectively, the samples were examined according to the same method as in example 1. A decomposition of the product could not be detected—except in the case of examples 15 and 16, which are not in accordance with the invention.

TABLE 2

Composition of the Matrices

| Example | Acid Polyacrylate | Basic Methacrylate | Physostigmine | Softeners | |
|---|---|---|---|---|---|
| 2 | 67% | 10% | 8% | 15% | 1-hexanol |
| 3 | 67% | 10% | 8% | 15% | 1-heptanol |
| 4 | 67% | 10% | 8% | 15% | 1-octanol |
| 5 | 67% | 10% | 8% | 15% | 1-decanol |
| 6 | 67% | 10% | 8% | 15% | 1-nonanol |
| 7 | 67% | 10% | 8% | 15% | 1-undecanol |
| 8 | 77% | 10% | 8% | 5% | 1-dodecanol |
| 9 | 67% | 10% | 8% | 15% | 1-dodecanol |
| 10 | 62% | 10% | 8% | 20% | 1-dodecanol |
| 11 | 67% | 10% | 8% | 15% | 1-tetradecanol |
| 12 | 67% | 10% | 8% | 15% | 1-pentadecanol |
| 13 | 67% | 10% | 8% | 15% | 1-heptadecanol |
| 14 | 72% | 10% | 8% | 10% | 1-dodecanol |
| 15 | 67% | 10% | 8% | 15% | propane diol |
| 16 | 67% | 10% | 8% | 15% | glycerin |
| 17 | 57% | 10% | 8% | 25% | 1-octyl dodecanol (1) |
| 18 | 67% | 10% | 8% | 15% | 1-oleyl alcohol | acid polymer: acrylate copolymer of 2-ethylhexyl acrylate, vinyl acetate and acrylic acid (AV of the dried pressure-sensitive adhesive: ca. 40)
basic methacrylate: cationic copolymerisate on the basis of dimethylaminoethyl methacrylate and neutral methacrylic esters (KOH value: ca. 180)
1-Nonadecanol and 1-eicosanol could not be incorporated under these conditions.

The adhesive forces were determined by way of experiments in accordance with the Test Specifications AFERA 4001 P. 11. The term adhesive force in this connection is used in the sense of the measured force necessary for peeling off a test sample having an area of 16 cm$^2$ from a steel plate at an angle of 90°. Each of the values stated is a mean value from determinations with five test samples at a time. In this connection, it is known to the skilled artisan that a good adhesive performance on human skin is mostly observed in those cases where TTS according to AFERA exhibit good adhesive behaviour.

TABLE 3

Adhesive force of the systems in dependence on the chain length of the softeners used as alcohols

| Example | Softener | Adhesive Force [N] |
|---|---|---|
| 1 | 25% triglycerides of medium-chain fatty acids DAB 9 | 3.01 |
| 2 | 15% 1-hexanol | 9.89 |
| 3 | 15% 1-heptanol | 9.73 |
| 4 | 15% 1-octanol | 5.70 |
| 5 | 15% 1-nonanol | 9.35 |
| 6 | 15% 1-decanol | 6.16 |
| 7 | 15% 1-undecanol | 5.13 |
| 9 | 15% 1-dodecanol | 5.53 |
| 11 | 15% 1-tetradecanol | 2.52 |
| 12 | 15% 1-pentadecanol | 1.03 |
| 13 | 15% 1-heptadecanol | 0.42 |

It can be seen from Table 3 that only the systems 11–13 exhibit a lower adhesive force than example 1. Furthermore, it is evident that as the chain lengths of the alcohols employed as softeners increase, the adhesive force becomes lower (the only exceptions are examples 3 and 7).

TABLE 4

Adhesive force seen in dependence on the portion of acid polyacrylate

| Example | 1-Dodecanol | Adhesive Force [N] | Acid Polyacrylate |
|---|---|---|---|
| 8 | 5% | 7.65 | 77% |
| 14 | 10% | 6.34 | 72% |
| 9 | 15% | 5.53 | 67% |
| 10 | 20% | 4.87 | 62% |

It is evident that the adhesive force increases with the rising portion of acid polyacrylate.

TABLE 4a

| Example | Softener | Adhesive Force [N] |
|---|---|---|
| 15 | 15% propane diol (1,2) | 13.27 |
| 16 | 15% glycerin | 12.74 |

TABLE 5

HLB values of the softeners

| | M | Mo | HLB = 20 $\left(1 - \frac{Mo}{M}\right)$ |
|---|---|---|---|
| triglycerides of medium-chain fatty acids DAB 9 | ca. 504 | M − 6 × 16 = 408 | 1.0* |
| methanol | 32.04 | 15.03 | 10.6 |
| ethanol | 46.07 | 29.06 | 7.4 |
| isopropanol | 60.10 | 43.0 | 5.7 |
| hexanol | 102.18 | 85.17 | 3.3 |
| heptanol | 116.20 | 99.19 | 2.9 |
| octanol | 130.22 | 113.21 | 2.6 |
| nonanol | 144.24 | 127.23 | 2.4 |
| decanol | 158.26 | 141.25 | 2.2 |
| undecanol | 172.28 | 155.27 | 2.0 |
| dodecanol | 186.3 | 169.29 | 1.8 |
| tetradecanol | 214.34 | 197.33 | 1.6 |
| pentadecanol | 228.36 | 211.35 | 1.5 |
| heptadecanol | 256.47 | 239.46 | 1.3 |
| nonadecanol | 284.73 | 267.25 | 1.2 |
| eicosanol | 298.55 | 281.54 | 1.1 |
| 2-octyl dodecanol | 298.55 | 281.54 | 1.1 |
| oleyl alcohol | 268.47 | 251.46 | 1.3 |
| glycerin | 92.10 | 41.08 | 11.1 |
| propane diol | 76.10 | 42.09 | 8.9 |

*value according to DAB 9 [German Pharmacopoeia, 9th ed.], Commentary S 3399.

What is claimed is:

1. In a transdermal therapeutic system for the administration of physostigmine to the skin, consisting of a backing layer impermeable to active substance, a pressure-sensitive adhesive reservoir layer containing 40 to 90 percent by weight polymeric material and 0.1 to 20 percent by weight physostigmine base or a pharmaceutically acceptable salt thereof, and a removable protective layer covering the reservoir layer, the improvement wherein the base material of the reservoir layer is polymeric material based on an acrylate and/or meth-acrylate and 0.1 to 40 percent by weight of a hydroxyl group-containing softener having an HLB value between 1.1 and 12.0, with the proviso that the softener is one which does not cause disintegration of the physostigmine base or salt thereof.

2. Transdermal therapeutic system according to claim 1, wherein the reservoir layer contains as polymeric material acrylate copolymers of 2-ethylhexyl acrylate, vinyl acetate and acrylic esters.

3. Transdermal therapeutic system according to claim 1, wherein the polymeric material based on methacrylates contains a copolymer based on dimethylaminoethyl methacrylate and neutral methacrylic esters.

4. Transdermal therapeutic system according to claim 1, wherein the softener is 1-dodecanol.

5. Transdermal therapeutic system according to claim 1, wherein the softener is 2-octyl dodecanol.

6. Transdermal therapeutic system according to claim 1, wherein the softener is oleyl alcohol.

7. Transdermal therapeutic system according to claim 1 wherein the softener is a linear or branched, saturated or unsaturated alcohol having 6 to 20 carbon atoms.

8. A process for the production of a transdermal therapeutic system according to claim 1, comprising applying, to an impermeable backing layer, a pressure-sensitive adhesive reservoir layer containing 40 to 90 percent by weight pressure-sensitive adhesive polymeric material and 0.1 to 20 percent by weight physostigmine base or a pharmaceutically acceptable salt thereof as active substance, and covering said layer with a removable protective layer, wherein for the reservoir layer there is used a homogeneous mixture of a polymer material based on an acrylate and/or methacrylate, and 0.1 to 40 percent by weight of a hydroxyl group-containing softener having an HLB-value between 1.1 and 12.0 with the proviso that the softener is one which does not cause disintegration of the physostigmine base or salt thereof.

9. Process according to claim 8, wherein the active substance is homogeneously mixed together with the components of the adhesive reservoir layer, optionally in solution, and spread onto the backing layer impermeable to active substance, whereafter the solvent or solvents—where present—are removed and, subsequently, the adhesive layer is covered with a protective layer, whereafter the laminate is manufactured into individual TTS by separating, which TTS are sealed into a packaging.

* * * * *